US012733965B1

(12) United States Patent
Stone et al.

(10) Patent No.: US 12,733,965 B1
(45) Date of Patent: Sep. 15, 2026

(54) JOINT DISLOCATION REDUCTION DEVICE AND METHOD

(71) Applicant: Stone Innovations LLC, Mill Valley, CA (US)

(72) Inventors: Kevin R. Stone, San Francisco, CA (US); Mark Joseph, Aspen, CO (US)

(73) Assignee: Stone Innovations LLC, Mill Valley, CA (US)

( * ) Notice: Subject to any disclaimer, the term of this patent is extended or adjusted under 35 U.S.C. 154(b) by 431 days.

(21) Appl. No.: 18/211,574

(22) Filed: Jun. 19, 2023

Related U.S. Application Data

(63) Continuation-in-part of application No. 17/817,415, filed on Aug. 4, 2022, now Pat. No. 12,440,626.

(60) Provisional application No. 63/259,699, filed on Aug. 4, 2021.

(51) Int. Cl.
*A61B 17/82* (2006.01)
*A61B 17/00* (2006.01)
*A61B 17/56* (2006.01)
*A61B 17/68* (2006.01)

(52) U.S. Cl.
CPC .... *A61B 17/82* (2013.01); *A61B 2017/00477* (2013.01); *A61B 2017/00871* (2013.01); *A61B 2017/00951* (2013.01); *A61B 2017/564* (2013.01); *A61B 2017/567* (2013.01); *A61B 2017/681* (2013.01)

(58) Field of Classification Search
CPC .............. A61B 17/842; A61B 17/8861; A61B 2017/0454; A61B 2017/12018
See application file for complete search history.

(56) References Cited

U.S. PATENT DOCUMENTS

| | | | | |
|---|---|---|---|---|
| 5,500,000 | A | 3/1996 | Feagin et al. | |
| 5,540,698 | A * | 7/1996 | Preissman | A61B 17/82 606/103 |
| 9,055,984 | B2 * | 6/2015 | Albertson | A61B 17/8869 |
| 9,173,647 | B2 * | 11/2015 | Bonutti | A61B 17/842 |
| 9,956,021 | B1 * | 5/2018 | Aebi | A61B 17/8861 |
| 10,433,890 | B2 * | 10/2019 | Golden | A61B 17/0469 |
| 11,395,688 | B2 * | 7/2022 | Chukinas | A61B 17/8863 |
| 11,478,275 | B2 * | 10/2022 | Smith | A61B 17/82 |

(Continued)

FOREIGN PATENT DOCUMENTS

| | | |
|---|---|---|
| WO | 2016154550 A1 | 9/2016 |

*Primary Examiner* — Anu Ramana
(74) *Attorney, Agent, or Firm* — Cozen O'Connor

(57) ABSTRACT

A joint dislocation reduction device includes an elongated flexible ribbon-like band extending along a central axis from a proximal end to a tapered distal end. A distal end coupling element is disposed at the distal end. A proximal end coupling element is disposed at the proximal end. A cord extends from the tapered distal end to a needle. In a form, the band includes a flexible metallic ribbon disposed within a surrounding flexible, insulating coating element, wherein the band includes one or more resilient shape-memory regions between the proximal and distal ends. With the band under applied axial tension, the proximal end cand distal end coupling elements are adapted to form a coupling assembly coupling the proximal and distal ends, forming a closed loop around a clavicle and a coracoid process with a single 180° twist, whereby the band rests flush against the clavicle and the coracoid process.

8 Claims, 11 Drawing Sheets

(56) References Cited

U.S. PATENT DOCUMENTS

| | | | | |
|---|---|---|---|---|
| 11,564,722 | B2 * | 1/2023 | Golden | A61B 17/3468 |
| 2023/0181226 | A1 | 6/2023 | Semingson et al. | |

* cited by examiner

Acromioclavicular Joint Structure

Acromioclavicular Joint Separation

JOINT DISLOCATION REDUCTION DEVICE AND METHOD

RELATED APPLICATIONS

This application is a continuation-in-part of nonprovisional U.S. patent application Ser. No. 17/817,415 filed Aug. 4, 2022, now U.S. Pat. No. 12,440,626 issued Oct. 14, 2025. U.S. patent application Ser. No. 17/817,415 in turn claims priority to U.S. Provisional Patent Application No. 63/259,699, filed Aug. 4, 2021. The aforementioned patent applications are incorporated by reference into the present application in their entirety.

TECHNICAL FIELD OF THE INVENTION

The present invention relates to medical devices designed for use during surgery, by stabilizing positions of bones and adjacent joint tissue during surgical procedures and during subsequent healing.

BACKGROUND

The human acromioclavicular joint, commonly referred to as the "AC joint", is one of the joints that constitute the human shoulder complex. It is formed by the top part of the shoulder blade (the "acromion") and the collar bone (the "clavicle"). Ligaments are soft tissue structures that support the acromioclavicular joint and include ligaments that connect the collar bone to a bony bump of the shoulder blade known as the "coracoid process" 28 (FIG. 1A).

Dislocated joints are of particular interest herein. The AC joint is a joint structure formed around a small gap (forming an almost-a-physical-"junction") between opposing ends of two elongated, generally horizontally extending bones in the shoulder, namely, the clavicle 16 (or "collarbone") and the acromion 27 which is a bone section which extends from the top part of the scapula 29. The scapula is otherwise a relatively wide, flat bone lying on the thoracic wall (the "shoulder blade"). In an intact shoulder, as shown in FIG. 1A, a small gap between the opposing distal ends of the clavicle and the acromion, is spanned by an acromioclavicular (or AC) ligament 24. A ligament known as the coracoacromial ligament (CCL) 24 attaches the acromion 27 to an upper portion of the scapula 29.

Again, in an intact shoulder, a coracoclavicular ligament formed by pair of nearly parallel and adjacent ligaments (the conoid ligament 22 and the trapezoid ligament 20) attach the clavicle 16 to an upper portion of the scapula 29 at the coracoid process 28. With all the ligaments intact, as well as the supporting musculature. the shoulder is generally stable and performs a "normal" function.

In a dislocated AC joint, as shown in FIG. 1B, for example, such as might occur pursuant to an injury during a vigorous sports activity, the AC ligament 24 and one or both coracoclavicular ligaments (often including both the conoid ligament 22 and the trapezoid ligament 20) may rupture. When that occurs, a distal end of the clavicle 16 which normally is held adjacent to the distal end of the acromion, breaks free and that end of the clavicle 16 is distracted from the shoulder blade pivoting "upward" from its normal, connected-by-the-AC-ligament to-the-acromion position. The affected shoulder no longer functions in a normal manner.

In order to repair such an injury, the clavicle must be aligned back to its normal position, with its distal end opposite the distal end of the acromion, and the three ruptured ligaments (conoid, trapezoid and AC ligament) must be repaired for long term success. The surgical procedures to effect the repair are difficult and, importantly, success requires that the distal ends of the clavicle and the acromion remain substantially aligned during the healing period.

The acromion and clavicle bone sections of the overall AC joint structure are normally mechanically coupled, albeit remaining separate bones. That mechanical coupling is effected by the resilient structure formed between opposing ends of the acromion and clavicle bone sections by the AC, conoid, and trapezoid ligaments collectively forming the overall AC joint. Prior art surgical repair methods, with sutures, tapes, and/or biological materials such as donor grafts, all fail to maintain adequate tension during healing, or cut through the bone due to their hardness. In prior art repairs, (1) sutures, tapes, or tissues have been wrapped around the tendon and bones at the dislocated joint, to effect reduction, or (2) screws have been drilled through the bones of joints to approximate them. None of those techniques reproduce the proper joint tension and maintenance of alignment without significant complications.

Among the difficulties encountered with the prior art techniques, hard materials or sutures may cut through the bones and soft tissues they are wrapped around as those elements stretch out during normal shoulder motion in rehabilitation after surgery. Screws and washers, when used, most often require a second surgery for their removal and often dislodge. These are all substantial disadvantages.

The subject invention utilizes a novel cable tie-like structure which permits improved joint reduction and maintenance of desired tension, effecting proper reduction during tissue healing.

DETAILED DESCRIPTION

Figure 1A:
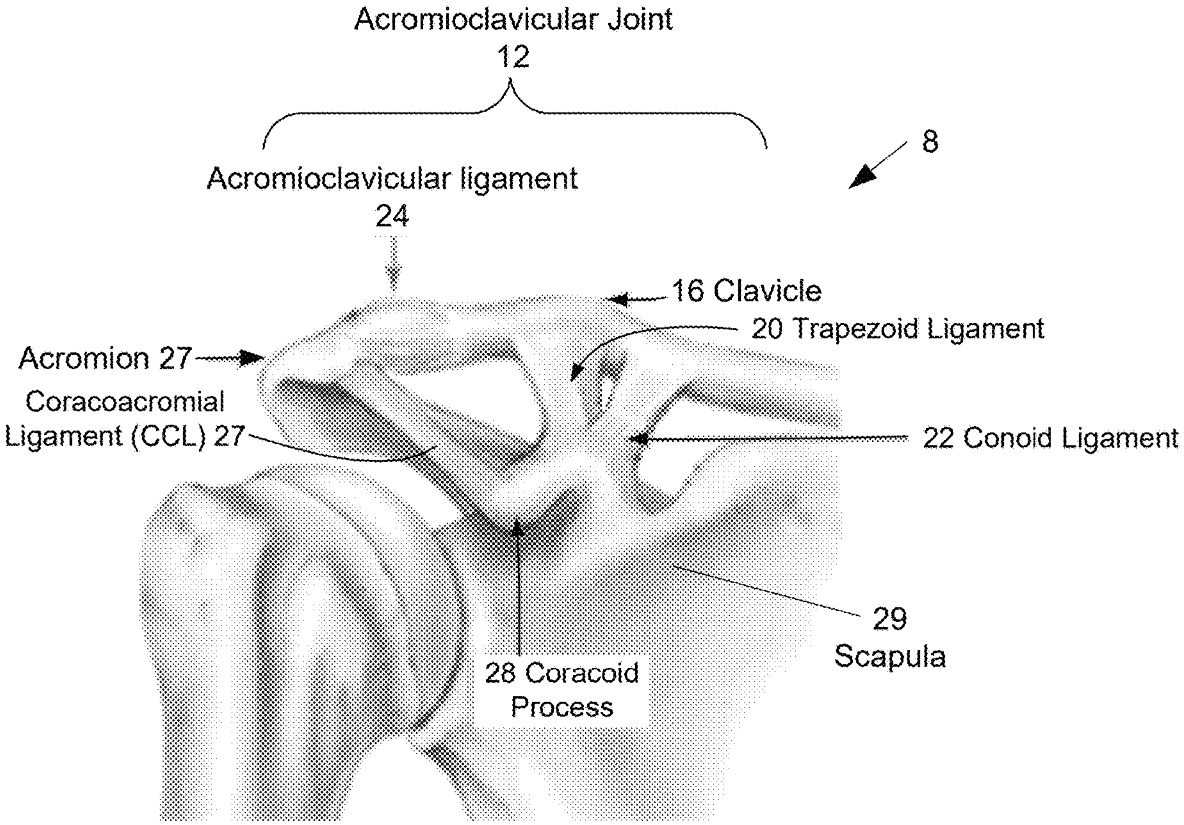
FIG. 1A shows the structure of an intact, undamaged shoulder.
Figure 1B:
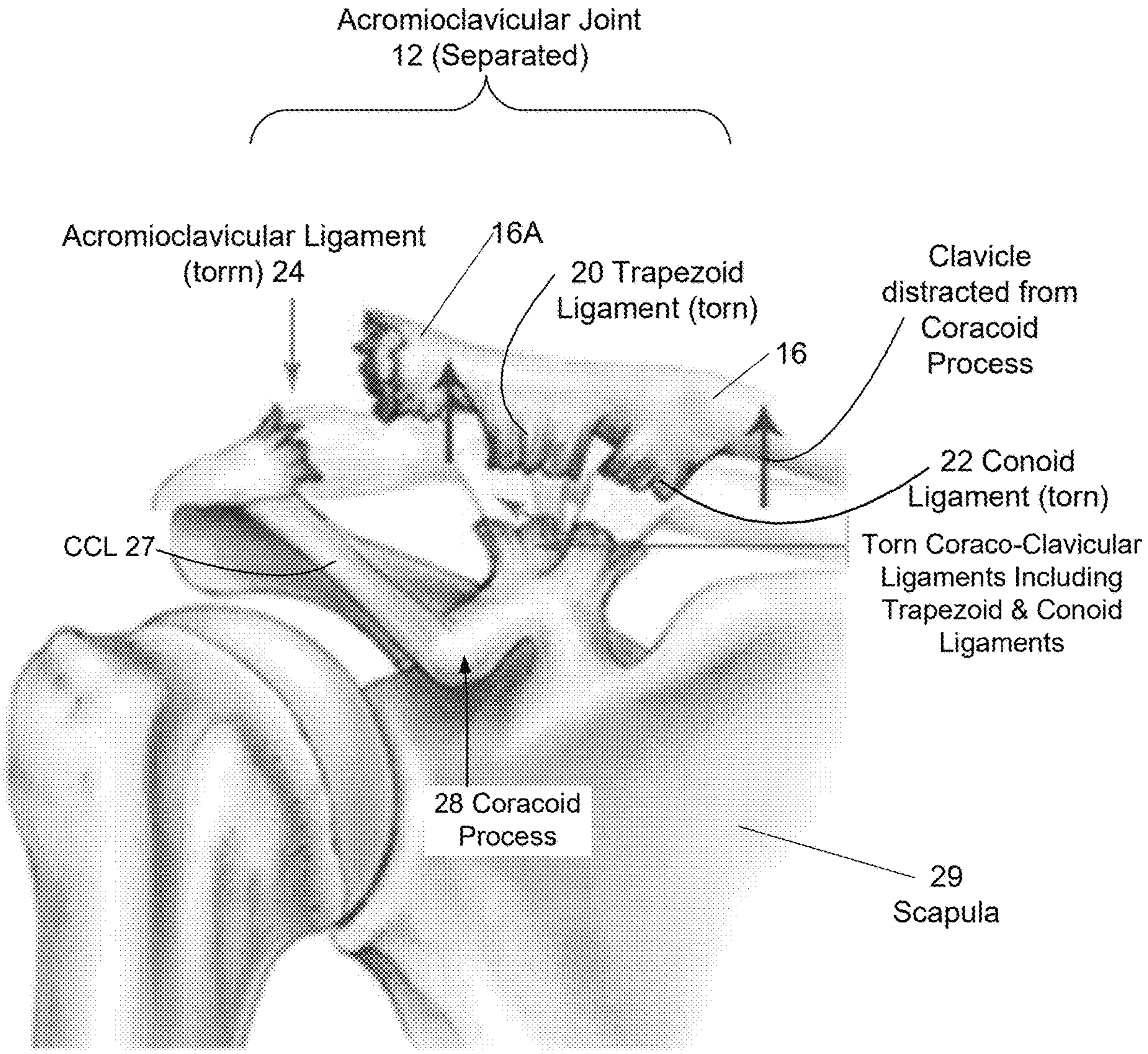
FIG. 1B shows the structure of a damaged, dislocated shoulder.

The structure of an intact, undamaged shoulder 8, including its acromioclavicular (AC) joint, 12 is shown in FIG. 1A. When such an AC joint is dislocated (or "separated"), as shown in FIG. 1B and indicated by reference number 14, typical changes in the structure include: (1) a distal end 16A of the clavicle 16 separates from the AC joint 12 and the clavicle 16 pivots upward with respect to its position in FIG. 1A, to the position shown in FIG. 1B, and (2) rupture occurs in at least one, and usually all, of the trapezoid ligament 20, the conoid ligament 22 and the acromioclavicular (AC) ligament 24 previously spanning the gap between the opposing ends of the acromion 27 and the clavicle 16, also as shown in FIG. 1B.

To repair the damage, and restore proper function to the shoulder, a surgical procedure is generally required. That procedure includes restoring the clavicle 16 to its normal position relative to the scapula 29 (including the acromion and coracoid process) and joining the torn ends of the respective ruptured ligaments 20, 22, and 24.

While conventional practice has the shortcomings mentioned above, the subject invention provides a structure and method which overcomes at least a significant portion of the difficulties of conventional surgical repair processes.

Figure 2:
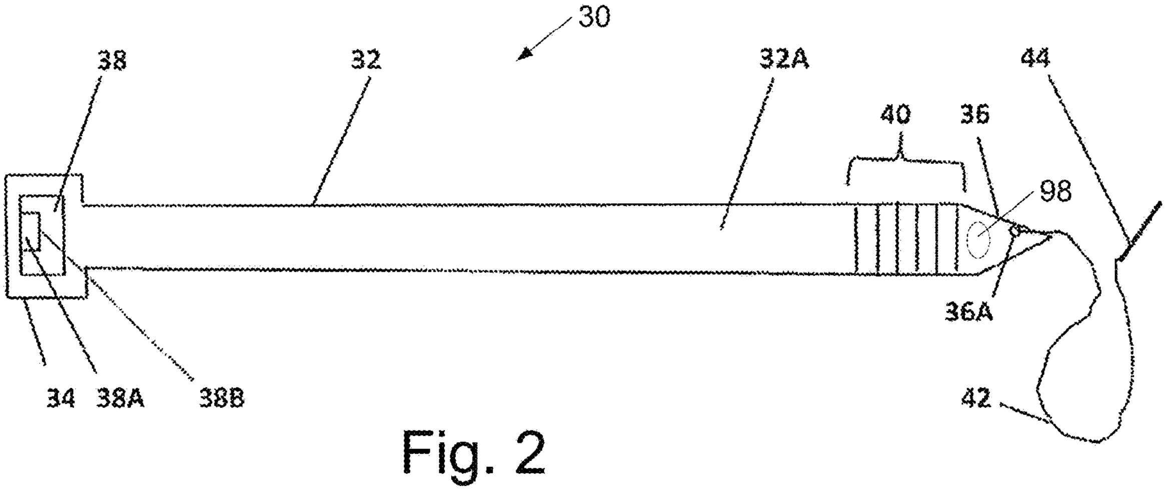
FIG. 2 shows a "modified cable tie"-like structure of the invention, prior to implantation.

In particular, a novel "modified cable tie"-like structure 30, exemplified by that shown in FIG. 2, is utilized to establish a desired, and near-normal, mutual orientation to the opposing distal ends of the acromion 27 and clavicle 16 and adjacent tissue of a dislocated AC joint 12 of FIG. 1B.

By way of example, FIG. 2 shows a top view of an exemplary modified cable tie-like structure 30 of the invention which is formed from an elongated band 32 of nylon (and preferably, Grilamid or Nylon 12), or hardened collagen, or a similar material, with a rectangle-like aperture 38 at a latch end 34 and an extended (and, preferably, tapered) lead end 36 opposite the latch end 34. A plurality of parallel ridges 40 are disposed on the top surface 32A of band 32, near the lead end 36, and extending transverse to a longitudinal axis of band 32. Aperture 38 includes a flexible latch portion 38A extending inward from the perimeter of aperture 38 to a lead edge 38B generally parallel to top surface 32A of band 32. Latch portion 38A is adapted to engage one of the ridges 40 as the lead end 36 passes through aperture 38, defining a closed loop formed by structure 30. Optimally, the material, and specific geometry, for band 32 is characterized by a coefficient of elasticity that matches (within ±25%) the net directional aggregate elasticity of the natural, undamaged acromioclavicular (AC), trapezoid and conoid ligaments of the human shoulder.

Figure 3:
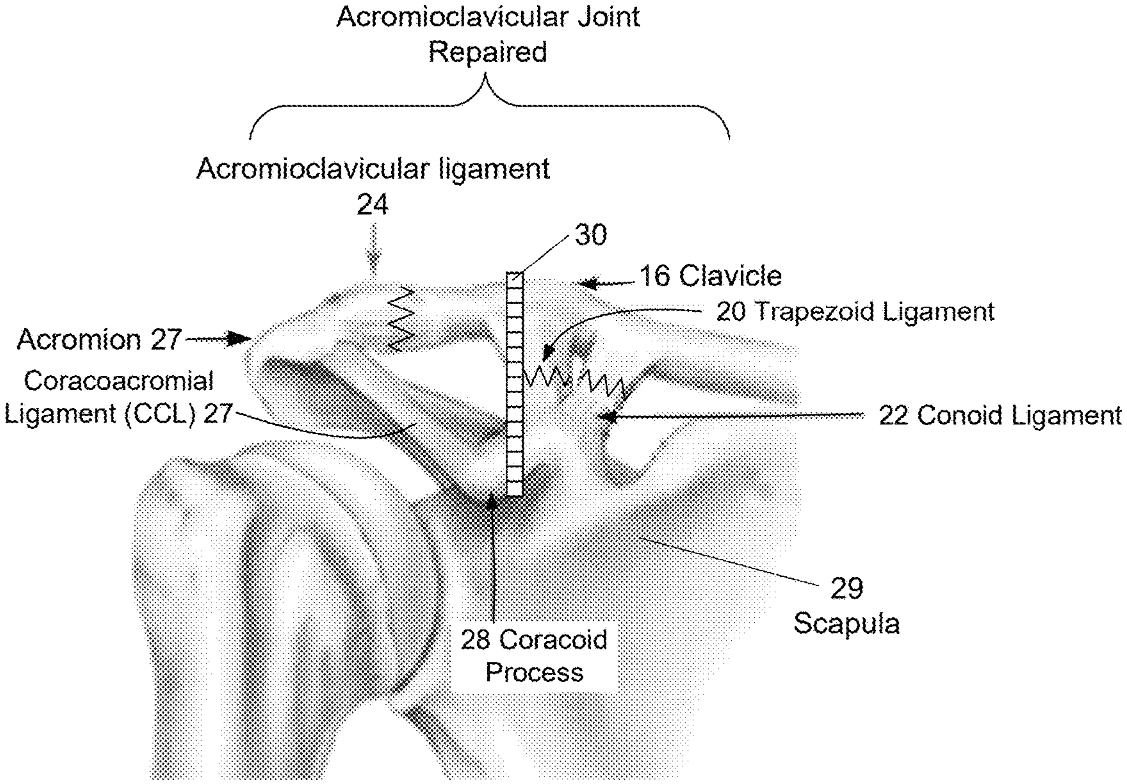
FIG. 3 shows a portion of an AC joint of a patient, with an implanted exemplar "modified cable tie"-like structure of the invention.

In a surgical repair procedure of the invention, the modified cable tie-like structure 30 is positioned to form an implanted closed loop, by drawing, under tension, the lead end 36 of structure 30 followed by band 32, around an angularly displaced distal portion of the clavicle 16 and the coracoid process 28, as shown in FIG. 3, to and through the rectangular-like opening 38 at latch end 34, with latch portion 38A interferingly engaging one of ridges 40 to close the loop. This cable tie-like structure is used in addition to repairing any ligaments of the AC 24, trapezoid 20, and coracoid 22 ligaments that may be torn.

The coracoid process 28 is an osseous projection from the neck of the scapula, forming a small hook-like structure protruding from a lateral edge of the superior anterior portion of the scapula 29.

In a normal shoulder 8, prior to an AC joint dislocation, the trapezoid and conoid ligaments 20 and 22 couple the coracoid process 28 to the clavicle 16 and the acromioclavicular (AC) ligament 24 mutually couple the opposed distal ends of the acromion 27 and the clavicle 16. As shown in FIG. 1B, following dislocation, generally all three of those ligaments rupture.

During the surgical repair procedure disclosed herein, as the lead end 36 of structure 30 passes above and around the clavicle and around an undersurface of the coracoid process, and to aperture 38 of latch end 34, to form the closed loop, the elongated band 32 is maintained under tension. As the loop is formed and tightened, that axially applied tension re-aligns the clavicle 16 with the acromion 27 substantially to their pre-dislocation positions. The biomechanical characteristics of the modified cable tie-like structure 30 effect a geometry and support structure for the acromion 27 and re-aligned clavicle 16 substantially matches those of the pre-dislocated AC joint 12. As a result, during the healing process, the various elements of the AC joint 12 enable the shoulder to function in a manner close to that of an undamaged shoulder 8. In particular, the support structure provided by modified cable tie-like structure 30 is characterized by similar (within ±25%) strength and net directional aggregate elasticity characteristics to those provided by the trapezoid and conoid ligaments 20 and 22 and the acromioclavicular ligament 24 prior to the dislocation, thereby allowing a degree of extension under stress and retraction when stress is removed.

As lead end 16 of the modified cable tie-like structure 30 passes into and through the rectangular aperture 38, forming the closed loop, an edge of the latch portion 38A of rectangular aperture 38 engages one of the steps or ridges 40 near the lead end 16, locking the position of band 32 and preventing the lead end 36 from pulling back out of the rectangular aperture 38. Together, the locking mechanism established by the engagement of latch portion 38A and one of ridges 40, causes band 32 to form a locked, closed, loop extending around the clavicle and the coracoid. The forward-facing portion of the loop formed by modified cable tie-like structure 30, is shown in FIG. 3.

When the modified cable tie-like structure 30 is to be installed about the clavicle 16 and the coracoid of the dislocated joint, as shown in FIG. 3, the modified cable tie-like structure 30 is introduced by its tapered end 36, and pushed and/or pulled through and wrapped around the angularly displaced clavicle 16 and the coracoid process under applied tension so that their distal ends of the clavicle 16 and acromion 27 are restored to their proper alignment, the nearby ruptured ends of the respective trapezoid, conoid, and AC ligaments 20, 22 and 22 are re-joined (preferably, by suturing) to complete the repair. In time, the repaired ligaments heal to maintain the proper alignment, and normal function is restored.

In a particular embodiment, the modified cable tie-like structure 30 includes near its tapered lead end 16, a string, band, or suture-like thread 24 extending from aperture 36A of lead end 36 with an optional (and preferably curved, but in some forms, straight) needle 44 at the distal end of thread 42. The needle 44 allows the surgeon to pass more easily (via pushing and/or pulling) the lead end 16 of the modified cable tie-like structure 30 around the clavicle and the coracoid to form the loop. As a consequence, as the lead end 16 of the band 32 is pushed and/or pulled (by the needle 24) through the rectangular aperture 38 of the locking mechanism and tightened, reduction in anatomic misalignment of the dislocated clavicle and the acromion is achieved. The elasticity of the band of the modified cable tie-like structure 30 enables tension to be applied so that those bones remain substantially aligned while permitting some relative motion, for example, in some embodiments 0.5-2 mm or as much a 6 mm is allowed. Preferably, the elasticity of the band 32 is such that near "normal" shoulder motion is accommodated during the healing process. With the band 32 implanted, inherent micro tension adjustment is possible so the system allows reasonable range of motion without substantial loss of position during the healing process. That range depends in part on the cross-section dimensions of the band. An optimal characteristic for a band 32, is one which matches net pre-rupture characteristics of the ligaments with which it might supplant during the healing process. Offsets from a perfect match work as well, but in a degraded fashion.

Unlike a "conventional cable tie", which is flexible, and thus adapted for wrapping around and holding cables together, the "modified cable tie"-like structure 30 of the invention, is not only flexible, but is also characterized by a desired elasticity. By way of example, a desired elasticity of novel band 32 permits longitudinal stretching of the band 32 when it is under tension during installation around clavicle and the coracoid of the dislocated joint. The ability to apply axial tension (for example, as much as 70 Newtons) to the tightening band around the dislocated bones, without causing collateral damage to the bones or nearby tissue, is important. It allows achievement of an optimal, or near-optimal, anatomic alignment, with small variations due to variations in patient anatomy, and maintenance of an optimal, or near-optimal, relative position of those elements, during healing. This feature provides a key advantage other methods of effecting healing of a dislocated AC joint. The biomechanical properties of the novel "modified cable tie"-like structure with a distinct elasticity coefficient, when implanted at the dislocated joint, allows the joint to move within a defined range of motion without being over tensioned in a manner which might be detrimental to healing. The breadth and stiffness (reflecting resistance to compression in response to an applied force) of the material of the "modified cable tie"-like structure with its characteristic elasticity, enables the joint to move within a defined range of motion during healing, without being over tensioned, and without danger of the material of the band (due to its breadth and stiffness) to resist, or preferably fully avoid, cutting through the bone. A preferred, although not absolutely necessary, material for the band 32 is a recently developed type of nylon known as Grilamid nylon or similar. An important characteristic of Grilamid nylon as it might be used for band 32, is that, after axially stretching under applied tension, upon removal of the tension its elasticity causes the band 32 to rapidly return to its length, or near that length, prior to the tension-induced stretching.

In some embodiments, rather than form the entire band of elastic material, the band at least one shape memory region, in some embodiments the shape memory regions have a crimped ziz-zag shape, in other embodiments the shape memory region have a corrugated shape.

In summary, the advantages of the disclosed structure are:

A. use of a "modified cable tie"-like structure for effecting bone (and adjacent tissue) and joint reduction, B. preferably there is a hole effected at the lead end 36 of the "modified cable tie"-like structure, which accommodates a length of elongated flexible material 42 attached to the lead end, allowing the surgeon to pull the lead end 36 around the bones and adjacent tissue during implantation, and C. The "modified cable tie"-like structure 30 is composed of material like nylon (and preferably, but not exclusively, Grilamid nylon or Nylon 12 or the like), collagen, lactides, polyethylene and polypropylene characterized by elasticity in a desired range, as well as resistance to breakage under tension up to 70 Newtons.

By way of example, the modified cable tie-like structure 30 of FIG. 2, has a rectangular cross-section (transverse to its principal axis). The dimensions can be in the range 4.8 mm±10% wide and 1.4 mm±10% thick, with an overall length preferably on the order of 25 cm.

The stiffness (related to a coefficient of elasticity) of the material of the modified cable tie-like structure 30 is generally within the range of the net of the three likely-to-be-ruptured trapezoid ligament 20, conoid ligament 22 and acromioclavicular (AC) ligament 24, or the equivalent. Typical values for those ligaments are set forth in Table 1:

TABLE 1

| | Intact CCL | Isolated Conoid | Isolated Trapezoid |
|---|---|---|---|
| Ultimate Load (N) | 500 +/− 134 | 394 +/− 170 | 440 +/− 118 |
| Yield Load (N) | 333N (SEM*, 40N) | n/a | n/a |
| Stiffness (N/mm) | 103 +/− 30 | 105 +/− 45 | 84 +/− 19 |

*SEM = standard error of the mean Values ±10% outside the respective ranges work as well although with reduced effect.

An exemplary embodiment of the "modified cable tie"-like structure 30 is shown in FIG. 2, prior to implantation. That exemplary structure 30 is shown in FIG. 3, implanted in a patient's AC joint 12.

In a preferred form, the ridged portion 40 of the structure 30 at a tapered lead end 36 (in common with a conventional cable tie structure) is adapted to engage the inside of a rectangular aperture 38 at the latch end 34 opposite the lead end 36 of the structure 30, (in common with a lock assembly of conventional cable tie structure). However, the modified cable tie-like structure disclosed herein, differs from conventional cable ties, particularly in that the modified cable tie-like structure 30 is characterized by a significantly greater "snap back" elasticity, whereby when stretched pursuant to applied tension and the, applied tension is removed, the "stretch" is reduced quickly, especially compared to conventional cable ties. That characteristic of the modified cable tie-like structure 30, which enables limited relative motion during patient recovery, is a primary factor in enabling satisfactory recovery following surgical repair of a dislocated AC joint.

Alternative joint dislocation reduction devices 50 are shown in FIGS. 6A-11, including many features of the joint dislocation reduction device 30 of FIGS. 2-3, plus additional features. The exemplary alternative joint dislocation reduction device 50 of FIGS. 6A-11 is shown and described in conjunction with an expanded view of an intact shoulder structure of FIG. 4 and an injured shoulder structure of FIG. 5. Device 50 is described in detail in conjunction with FIGS. 6A-11.

Figure 4:
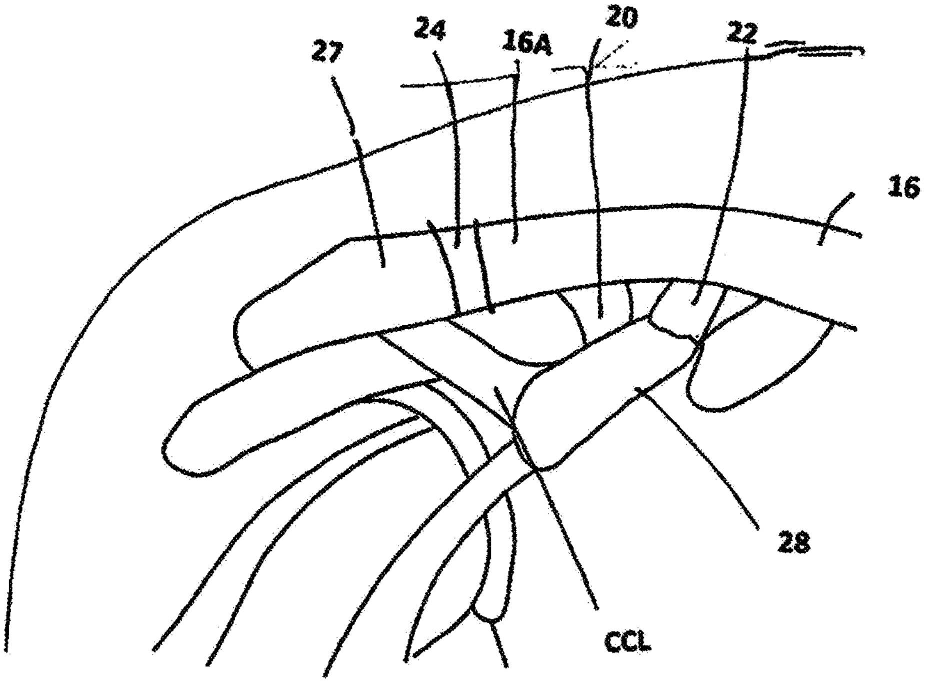
FIG. 4 shows a large-scale line drawing of the structure of an intact, undamaged shoulder.
Figure 5:
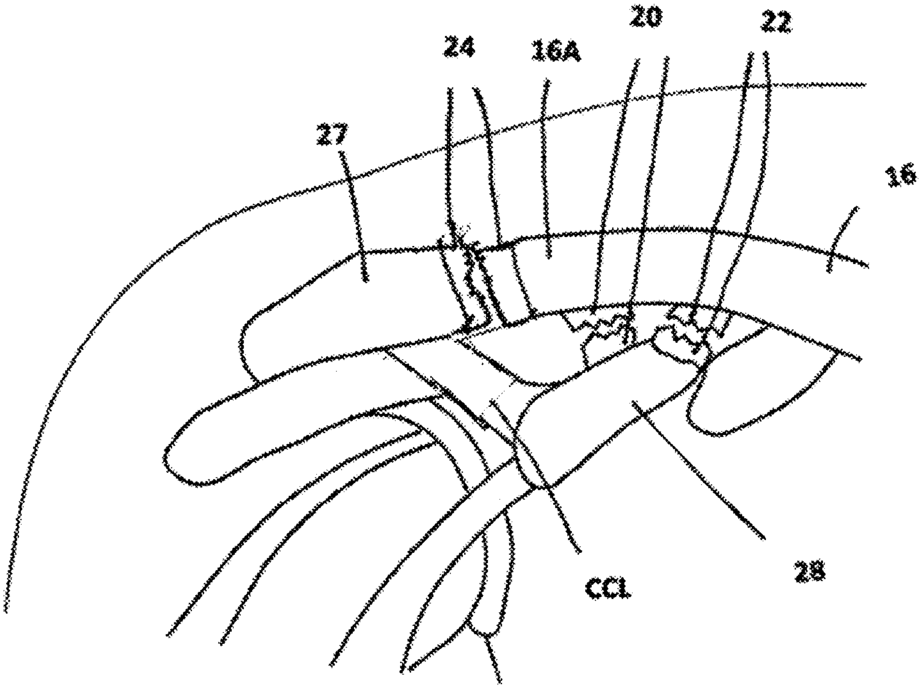
FIG. 5 shows a large-scale line drawing of the structure of a damaged, dislocated shoulder, including three ruptured ligaments.
Figure 6A:
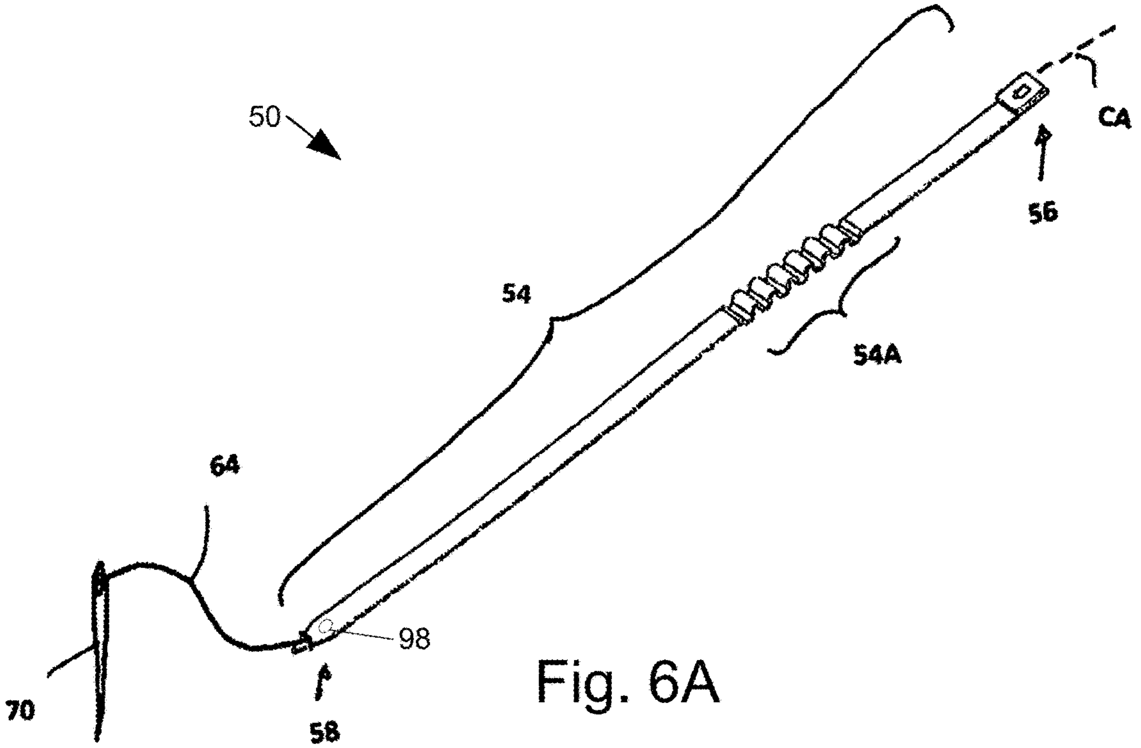
FIGS. 6A, 6B, 6C, and 6D show an alternative form of a "modified cable tie"-like structure of the invention, prior to implantation, in an isometric view 6A (with a needle and suture at the lead end), a side view 6B (without a needle and suture at the lead end), a top view 6C (without a needle and suture at the lead end), and 6D illustrates a clamping device that may secure the modified cable tie-like device in a loop.
Figure 6B:
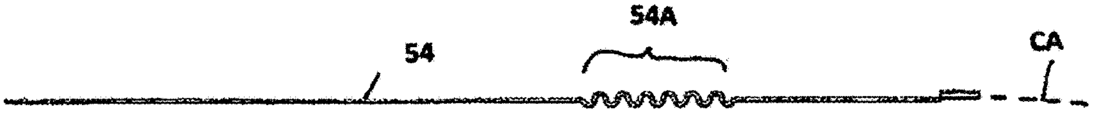
Figure 6C:
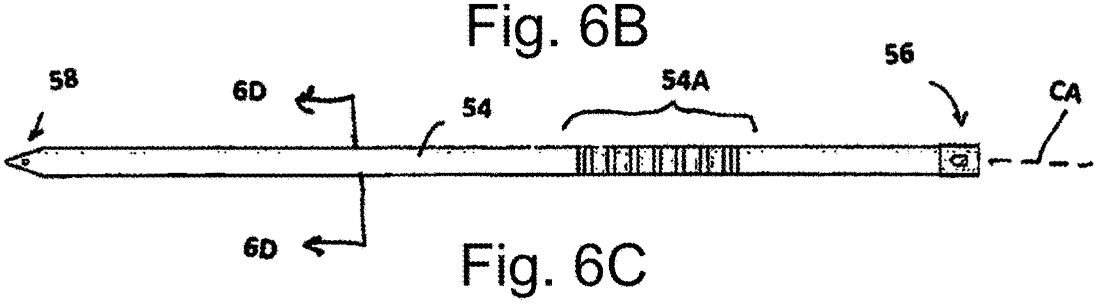
Figure 6D:
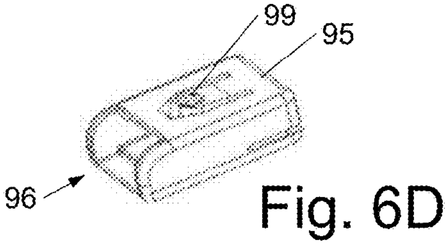
Figure 7:
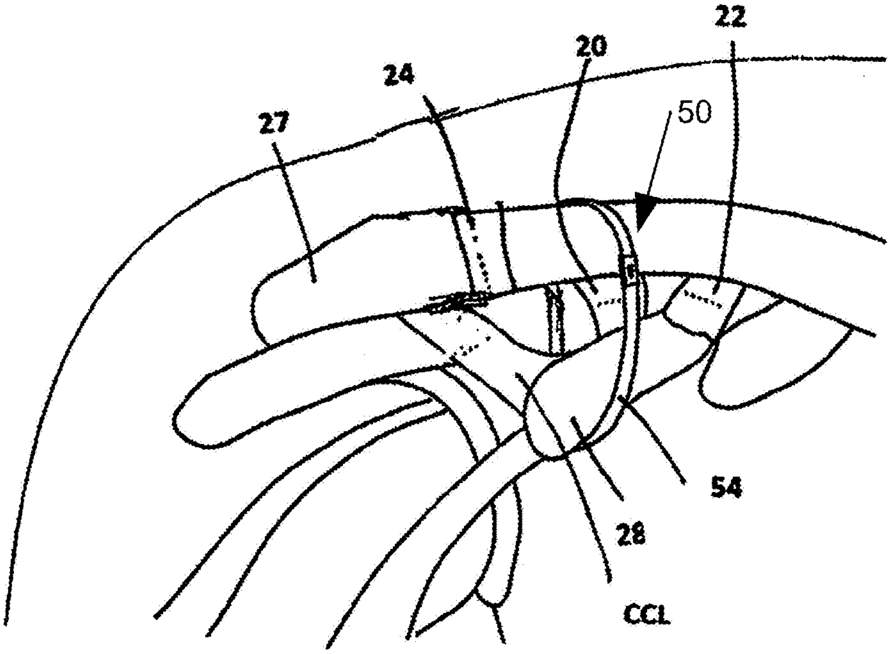
FIG. 7 shows the alternative "modified cable tie"-like structure of FIGS. 6A-6D in a "closed loop" disposed about body parts in the damaged shoulder of FIG. 2.

FIGS. 4 and 5 correspond to initial FIGS. 1A and 1B, where FIG. 4 represents an enlarged depiction of the intact Acromioclavicular Joint of FIG. 1A, and FIG. 4 represents an enlarged depiction of the separated/injured Acromioclavicular Joint of FIG. 2. FIG. 7 represents an enlarged depiction of the separated/injured Acromioclavicular Joint of FIG. 2 after that joint has been surgically repaired using the devices and methods disclosed herein. The various tissues and bones of FIGS. 4, 5 and 7 are identified with the same reference designations as are the corresponding bones and tissues of FIGS. 1A and 1B.

FIGS. 6A-6D, 7 and 8 illustrate an alternative joint dislocation reduction device 50 which principally includes an elongated flexible band 54 extending along a central axis CA from a proximal end 56 to a distal end 58. The band 54 comprises a ribbon-like metallic core 60 (with a length in the range 150 to 250 mm and preferably having a rectangular cross-section extending transverse to the central axis CA). Preferably, the rectangular cross-section of band 54, including the covering 80, is 0.75 to 1.5 mm×4 to 7 mm×6 mm±20%. Band 54 is in some embodiments constructed of spring stainless steel, in another embodiment titanium, although other materials may be used such as spring steel, and other metals. The distal end 58 is tapered and includes, extending therefrom, a cord 64, or drawstring, terminating in a curved or straight needle-like structure 70.

Figure 9:
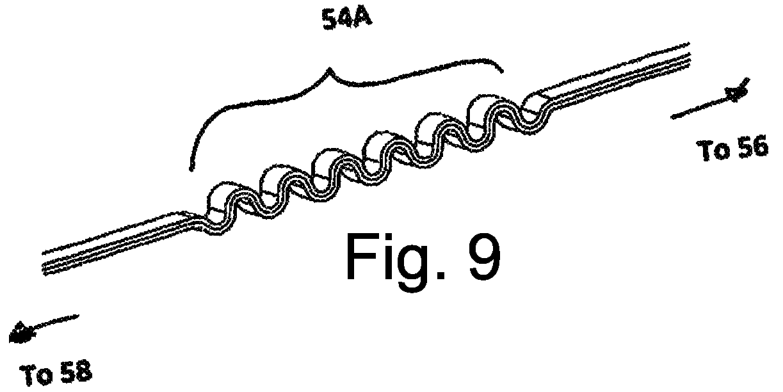
FIG. 9 shows an exemplary resilient spring element in the band of the "modified cable tie"—like structure of FIGS. 6A-6D.
Figure 10:
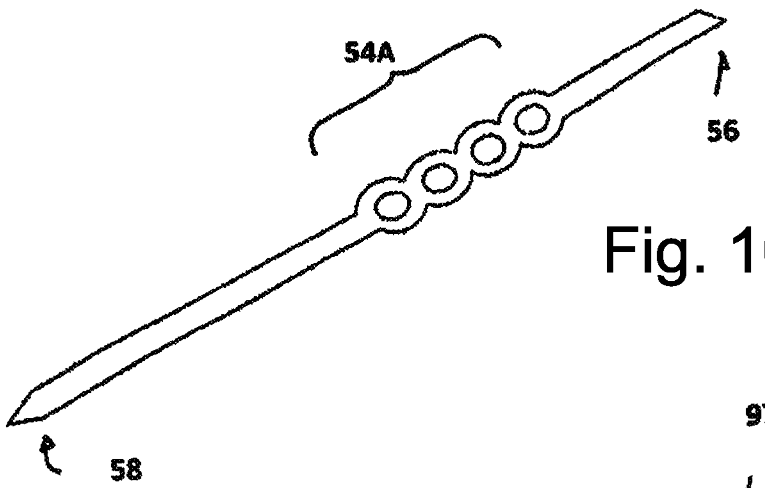
FIG. 10 shows an alternative exemplary resilient spring element adapted for deployment in the band of the "modified cable tie"-like structure of FIGS. 6A-6D.

The band 54 is disposed within a surrounding biocompatible and flexible coating 80. The coating 80 may be a polymer, for example, made of PTFE, PEEK, PET, HDPE, polyurethane of other polymer in the range of shore durometer 70A to 90A and as hard a shore GOD. The coating can be applied as shrink tubing with an adhesive moisture barrier inner coating that adheres to, and seals to, the band 54 when heated and shrunk down. Other means may be used to apply the polymer coating 80 such as injection over-molding, sheet compression molding or other means to durably cover the band 54 and protect bones and ligaments from abrasion. At least one region of the band is characterized as having a shape-memory, being spring-like in the direction of the central axis so that in response to axially-applied tension which axially stretches the coated core 60/80, the coated core 60/80 rapidly returns to its rest length upon cessation of the applied tension. By way of example, FIGS. 9 and 10 illustrate two forms for the metallic shape-memory regions 54A. Each form provides the axial stretching needed for operation. As illustrated in FIGS. 6A-6D, core 54 includes a single region 54A characterized by the above-described shape-memory. The coating 80 is flexible enough so that it flexes with the band 54 allowing axial stretching. In other embodiments, there may be more than one such region. In a particular embodiment 8, the band 54 has a 180-degree twist to better allow conformity to surfaces of the coracoid and clavicle; in yet another embodiment the band 54 has a 360-degree twist to allow conformity to anatomic surfaces.

Figure 8:
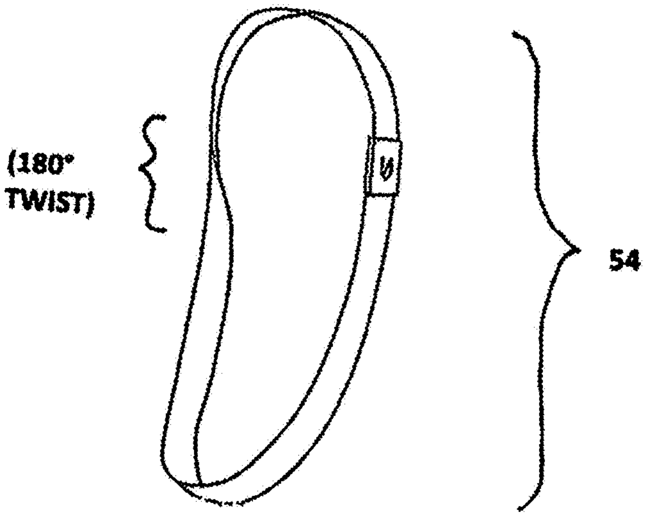
FIG. 8 shows the alternative "modified cable tie"-like structure of FIGS. 6A-6D in a "closed loop" but not deployed about body parts in the damaged shoulder of FIG. 2.

FIG. 7 illustrates utilization of band 54 in a surgical procedure, wherein the band 54 is formed to a closed loop about the clavicle 16 and the coracoid process 28, and is tensioned to position the ruptured ligaments 20, 22 and 24, in mutual alignment so that the ends of the ruptured tendons can be rejoined (preferably by suturing). Moreover, as described below, the tensioned closed loop band 54 has appropriate stretch/resilience to permit small circumferential movement during healing. of particular import, as shown in FIG. 8, the closed loop formed by band 54 includes a single 180° twist so that the "flat" moebius-like ribbon band has surfaces which are angled so that it lies "flat" against both the clavicle 16 and the coracoid process 28, placing the bones and tissues of the shoulder in an optimal position for healing while allowing the patient to "use" the AC joint 8 as it heals.

Figure 11:
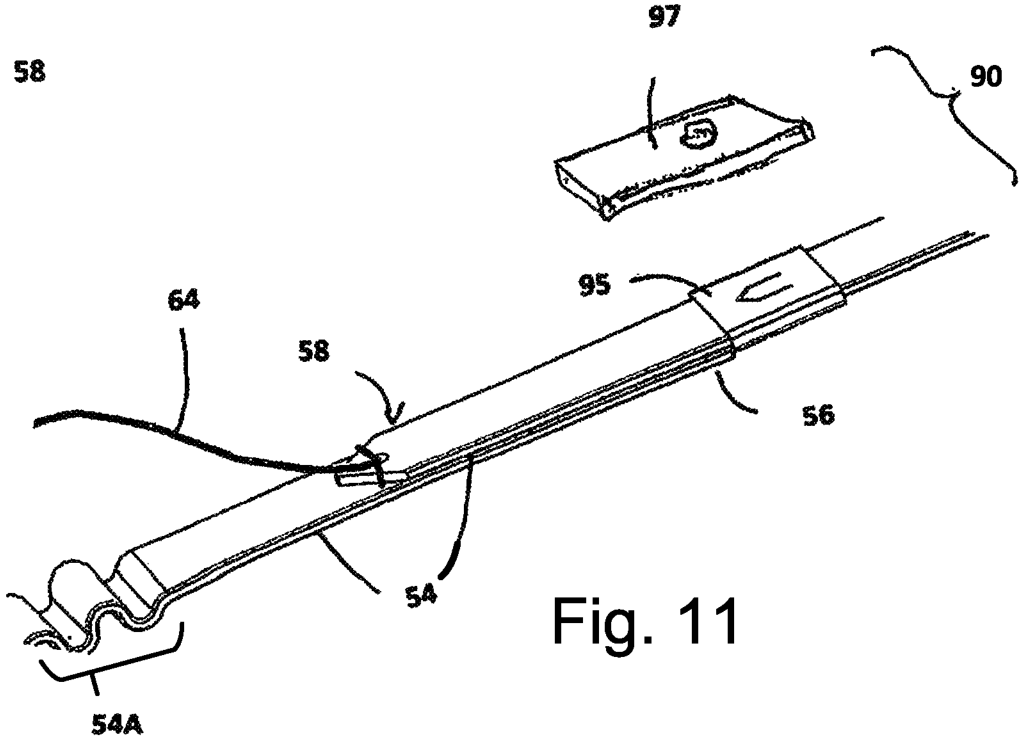
FIG. 11 shows an exemplary coupling assembly coupling proximal and distal ends of the "modified cable tie"-like structure of FIGS. 6A-6D.

FIG. 11 illustrates an exemplary latch assembly 90 which joins the proximal end 56 to the distal end 58. As shown, distal end 58 of band 54 overlaps proximal end 56, and the overlapping ends pass (in opposite directions) through a crimp connector 95 which is adapted to mechanically crimp the overlapping ends within the clamp 95. A flexible outer element 97, preferably of the same material as the coating 80, is affixed to the crimp connector to cover any metallic outer surface of the crimp connector 95.

Figure 12:
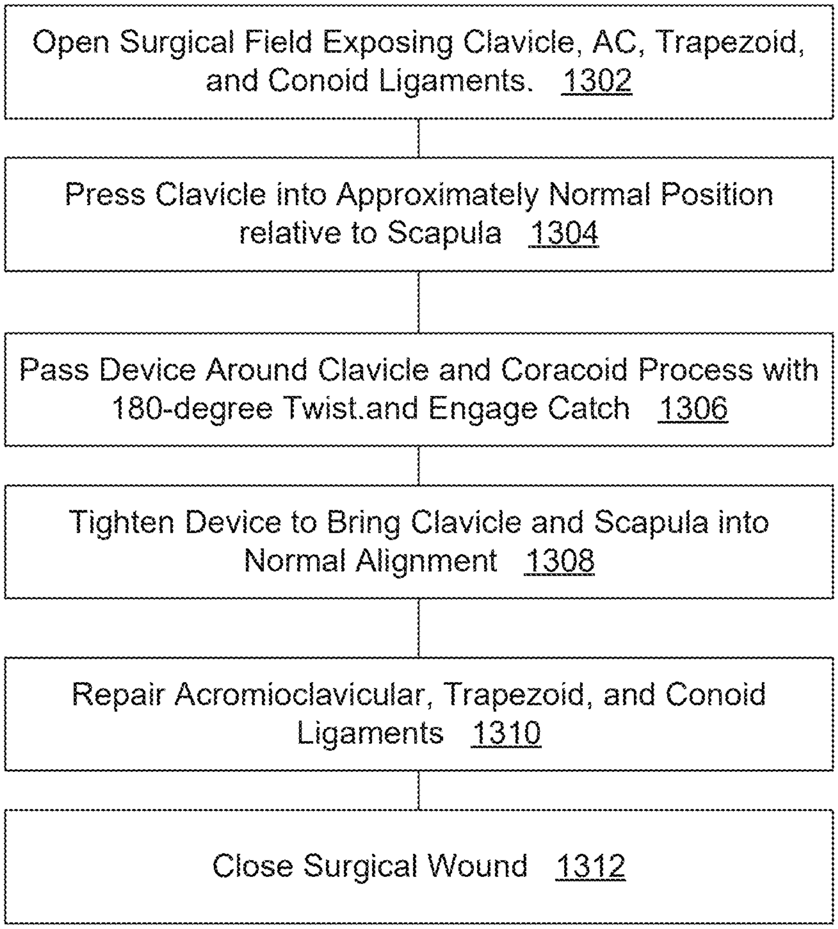
FIG. 12 shows a flowchart of repairing a dislocated acromoclavicular joint with the "modified cable tie"-like structure herein disclosed.

The device herein described is used in a method outlined in FIG. 12. First, a surgeon exposes key parts of the acromioclavicular joint 1302 including exposing the ACL, the trapezoid, and conoid ligaments. He then brings 1304 the clavicle into approximate position relative to the scapula and passes 1306 the modified cable-tie device herein described around the clavicle and coracoid process; in some embodiments using a 180 degree twist forming a in the modified cable-tie device to form a moebius-like loop and to better fit contours of the clavicle and coracoid process. The surgeon engages the coupler 95 illustrated in FIG. 6D stabilize the device in position. The surgeon then tightens 1308 the device to an appropriate patient-dependent tension thereby bringing the clavicle and scapula into better alignment and hold this alignment while the ligaments are repaired; the surgeon then crimps the coupler 95 to hold the device as a fixed loop. Then the surgeon repairs 1310 the ACL, Trapezoid, and conoid ligaments (usually by suturing). Once the device is in place and properly tightened, and the ligaments repaired, the surgeon closes 1312 the surgical wound. Additional steps may also be included such as administration of anesthesia and prophylactic antibiotics.

Figure 13:
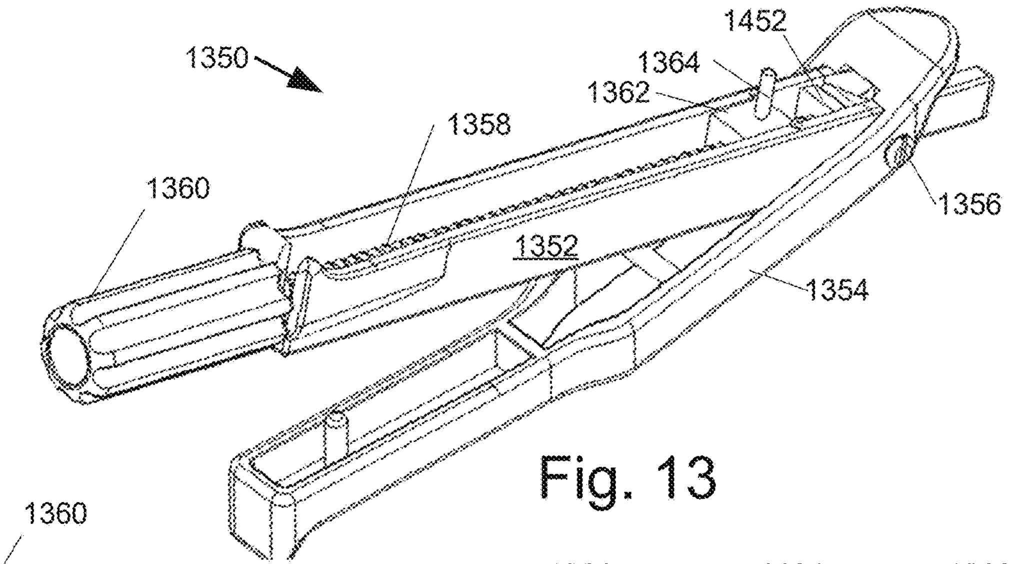
FIG. 13 is a perspective view of a tool for installing the modified cable-tie-like device herein described.

Once the modified cable-tie like device of the present invention has been passed around a patient's acromion and clavicle, it may be tightened and the crimp coupler or connector 95 (FIG. 6D or 11) crimped with the tightening and crimping tool 1350 illustrated in FIG. 13 to hold the device as a loop of a determined circumference.

In embodiments, the tool of FIG. 13 has a first jaw portion 1352 (FIGS. 13, 16, 17, and 18) and a second jaw portion 1354 pivotably held together by a pin or screw 1356.

Within first jaw portion 1352 is a rotatable screw 1358 coupled to a handle 1360. Slideably engaged within first jaw portion 1352 and engaged with threads of rotatable screw 1358 is a nut 1362 having a hook or pin 1364. A crimping jaw 1366 is fitted to second jaw portion 1354.

First jaw portion 1352 has a bottom slot 1450 (FIGS. 17 and 18) of width sufficient to allow free end 1404 of the cable-tie-like device 1402 to fit through it, but narrow enough that the connector 95 does not fit through the slot 1450. First jaw portion 1352 also has a pivot 1454 attached to a wall 1452 against which rotatable screw 1358 may bear.

First jaw portion 1352 also has a recess 1456 (FIGS. 18 and 16) at its slotted end configured to slideably engage with crimp connector 95.

The modified cable-tie-like device is engaged at one end with connector 95. In embodiments, this engagement may be welded, riveted, or fitting a free end 1404 and narrow body of the cable-tie-like device through a slot in connector 95 but a widened end of the cable-tie-like device that will not fit through the slot. Connector 95 has a slot 96 through which a free end 1404 of modified cable-tie-like device 1402 fits.

Figure 14:
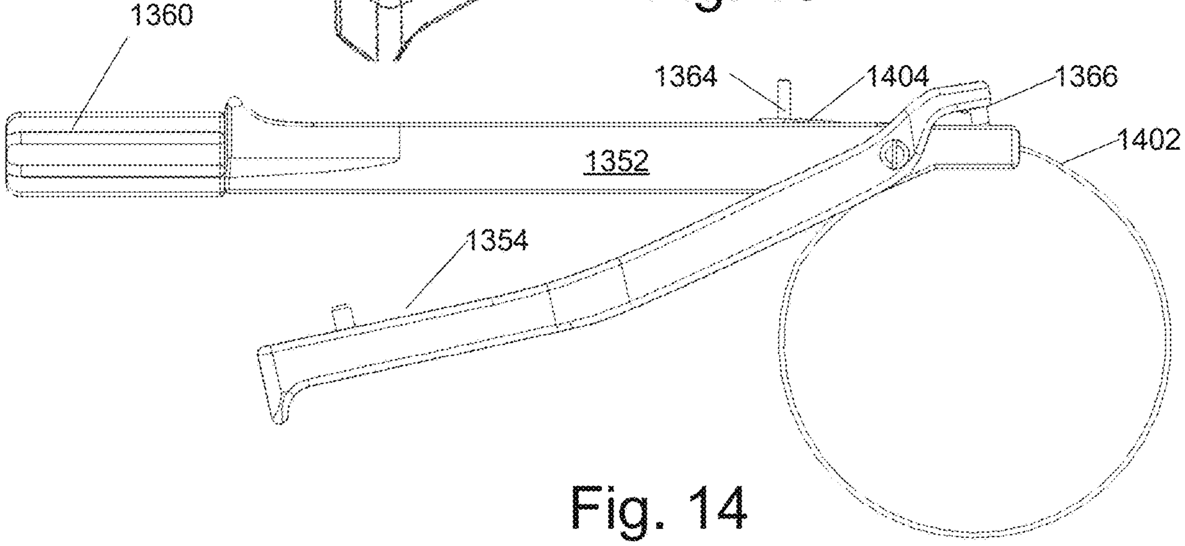
FIG. 14 is a side view of the tool of FIG. 13.
Figure 15:
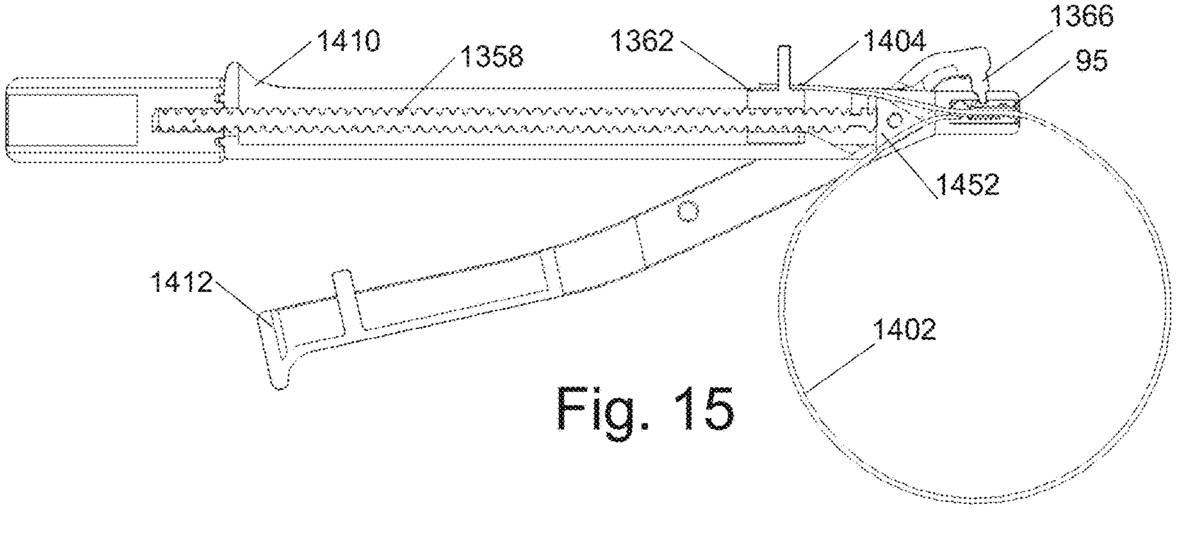
FIG. 15 is a cutaway view of the tool of FIG. 14.
Figure 16:
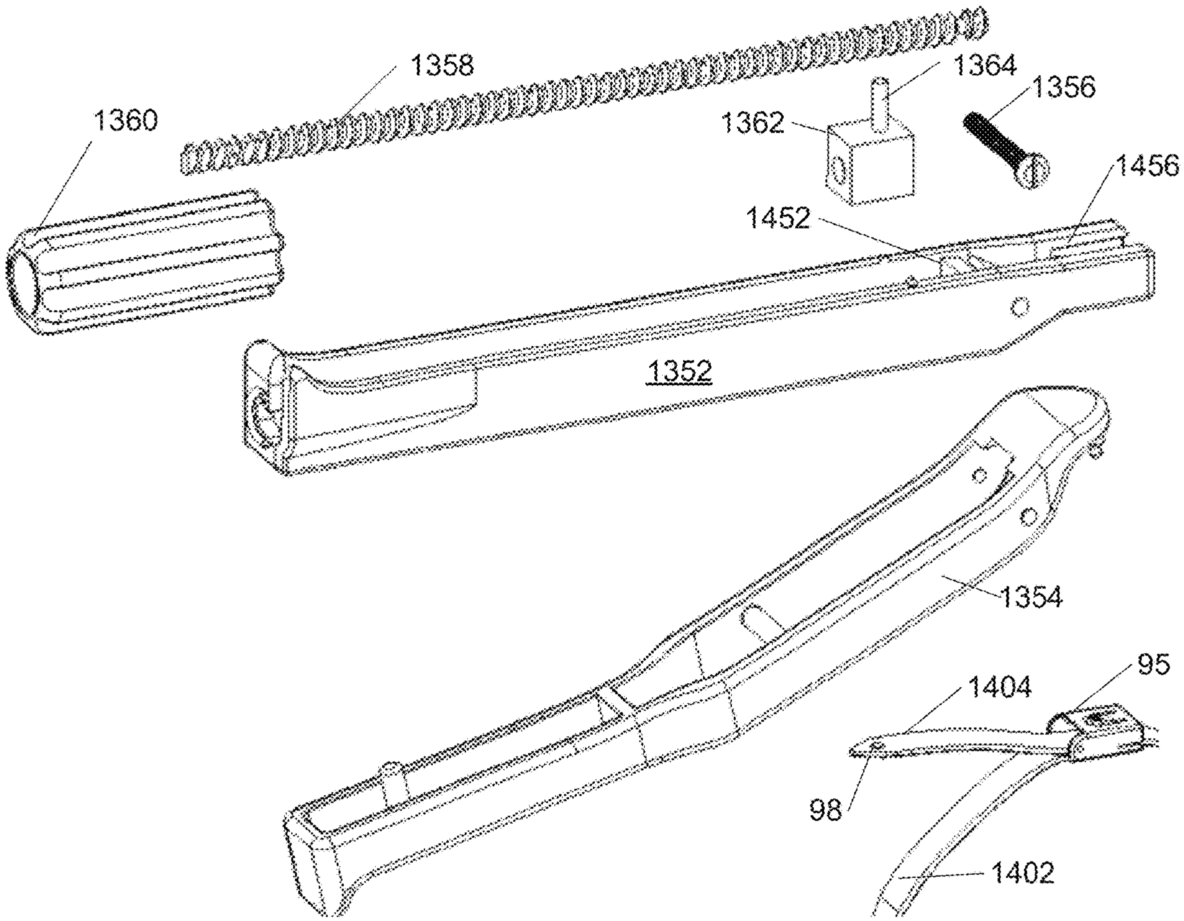
FIG. 16 is a perspective view of component parts of the tool of FIG. 13.
Figure 17:
FIG. 17 is a bottom view of first jaw portion 1352, showing a slot in its bottom at the modified-cable-tie end that is wide enough to pass the modified cable-tie like device but too narrow to pass the crimp connector.
Figure 18:
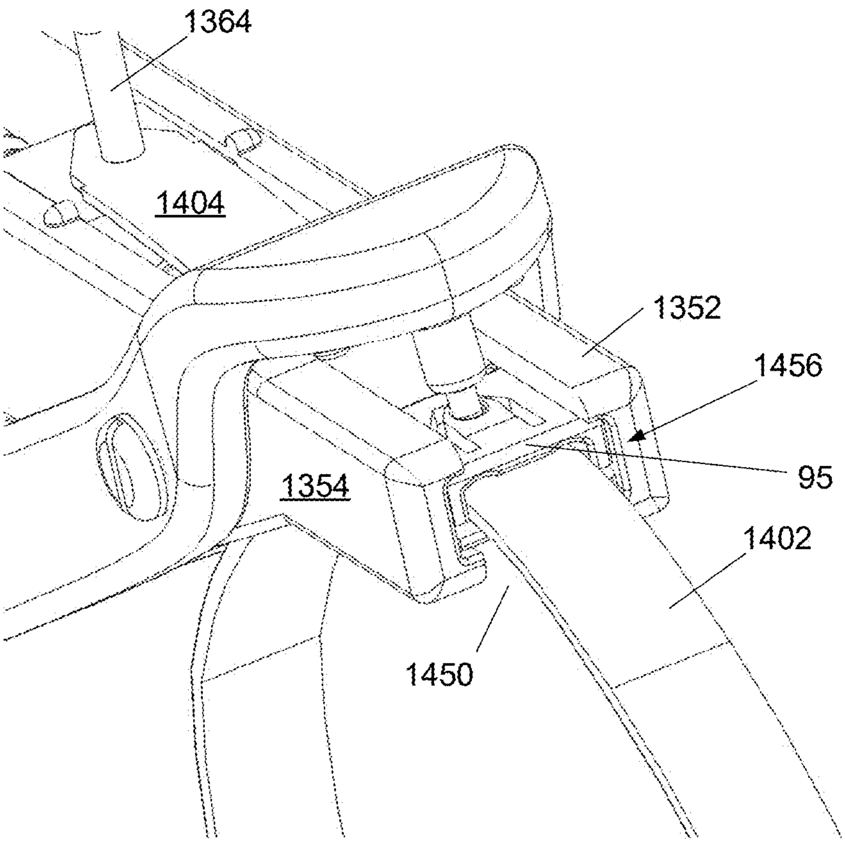
FIG. 18 is a perspective view of the modified-cable-tie end of the first jaw portion.

When the modified cable-tie-like device 1402 (FIGS. 14 and 15) of the present invention is used with tool 1350, the device is inserted around the acromion and clavicle as previously described, with any necessary twists (twists are not shown in FIG. 14) and the end distal from the connector is threaded through crimp connector 95; a hole 98 (FIGS. 2 and 6A) in the end distal from the connector is then fit over hook or pin 1364 as shown in FIG. 14. Screw 1358 is rotated, drawing the nut 1362 and pin 1364 away from crimp connector 95, to tighten the modified cable-tie-like device to an appropriate tension before the surgeon squeezes the handle ends 1410, 1412 of first jaw portion 1352 and second jaw portion 1354 together thereby forcing crimping jaw 1366 into crimp connector 95 and permanently securing the modified cable-tie-like device into a loop.

Once crimp connector 95 is crimped, rotation of the screw 1358 is reversed permitting disengagement of the hole 98 in the modified cable-tie-like device 1402 from hook or pin 1364; after which the tool 1350 may be slid off crimp connector 95 and the loop portion of modified cable-tie-like device 1402 slips through the slot permitting withdrawal of the tool 1350 from the patient.

In some embodiments, crimp connector 95 has a tab portion 99 that is compressed into the modified cable-tie-like device 1402 by crimping jaw 1366.

Installation of the cable-tie-like device 1402 is therefore accomplished by working the tapered free end of the device around the acromion and clavicle of the associated AC joint with any necessary twists and the second end of the device held in crimp connector 95. Then the free end of the device is threaded through a slot of the crimp connector and the tightening-crimping tool discussed with reference to FIGS. 13-18 is inserted over the crimp connector with the crimp connector securely held in recess 1456, a body of the device dropped through slot 1450, and free end 1404 of the device inserted over pin 1364. The screw is then rotated to tighten the device to a desired tension and the first and second jaw portions are squeezed to crimp the crimp connector. The screw is then rotated in a reverse direction to loosen the device so the free end 1404 can be removed from pin 1364, whereupon the crimp connector 95 can be slid out of recess 1456 and the tightening-crimping tool removed from the surgical wound.

Although the foregoing descriptions of the embodiments of the present technology contains some details for purposes of clarity of understanding, the technology is not limited to the detail provided. There many alternative ways of implementing the technology. The disclosed embodiments are illustrative and not restrictive.

What is claimed is:

1. A method of reducing a dislocation of an acromio-clavicular joint comprising:

inserting a first end of a dislocation reduction device around both an acromion and a clavicle associated with the acromio-clavicular joint, the first end of the dislocation reduction device being tapered and having a hole configured to fit over a pin of a tightening-crimping tool, a second end of the dislocation reduction device coupled to a crimp connector having a slot adapted to receive the first end of the dislocation reduction device;

passing the first end of the dislocation reduction device through a slot of the crimp connector;

tightening the dislocation reduction device;

crimping the crimp connector to form the dislocation reduction device into a loop.

2. The method of claim 1 further comprising passing the hole of the first end of the dislocation reduction device over a pin of the tightening-crimping tool, the pin of the tightening-crimping tool coupled to a nut configured to be driven by rotation of a screw;

rotating the screw in a first direction of rotation to tighten the dislocation reduction device; and crimping the crimp connector to secure the crimp connector to the first end of the dislocation reduction device and thereby form a permanent loop in the dislocation reduction device.

3. The method of claim 2 further comprising rotating the screw in a second direction of rotation to release tension on the dislocation reduction device to permit loosening of the dislocation reduction device to the desired tension before crimping the crimp connector to secure a permanent loop in the dislocation reduction device.

4. The method of claim 3 wherein the tightening-crimping tool has, at a first end of a first member, a recess to retain the crimp connector and a slot wide enough to pass a body of the dislocation reduction device but too narrow to permit passage of the crimp connector.

5. The method of claim 4 wherein the permanent loop of the dislocation reduction device has a 180-degree twist.

6. The method of claim 4 wherein the dislocation reduction device is formed of titanium or stainless steel with a biocompatible polymeric coating, and where the dislocation reduction device has at least one portion of shape memory with a corrugated or zig-zag shape relative to a central axis of the dislocation reduction device.

7. The method of claim 4 wherein the permanent loop of the dislocation reduction device has a 360-degree twist.

8. The method of claim 4 further comprising repairing an acromioclavicular ligament and one or both coracoacromial ligaments if ruptured.

* * * * *